(12) United States Patent
Sekiya et al.

(10) Patent No.: US 7,380,485 B2
(45) Date of Patent: Jun. 3, 2008

(54) CLEANING TOOL

(75) Inventors: Kennichi Sekiya, Kobe (JP); Masahide Kaneko, Shinagawa-ku (JP); Shinnichi Kadode, Kaga (JP)

(73) Assignee: KB Seiren, Ltd., Sabae, Fukui (JP)

( * ) Notice: Subject to any disclaimer, the term of this patent is extended or adjusted under 35 U.S.C. 154(b) by 820 days.

(21) Appl. No.: 10/492,195

(22) PCT Filed: Oct. 11, 2002

(86) PCT No.: PCT/JP02/10639

§ 371 (c)(1),
(2), (4) Date: Apr. 20, 2004

(87) PCT Pub. No.: WO03/035286

PCT Pub. Date: May 1, 2003

(65) Prior Publication Data

US 2005/0016564 A1    Jan. 27, 2005

(30) Foreign Application Priority Data

Oct. 23, 2001 (JP) .............................. 2001-325149
Aug. 21, 2002 (JP) .............................. 2002-241009

(51) Int. Cl.
*D04C 1/00* (2006.01)
(52) U.S. Cl. ............................................................ 87/8
(58) Field of Classification Search ................ 87/8, 87/9; 15/1.51, 1.52, 160
See application file for complete search history.

(56) References Cited

U.S. PATENT DOCUMENTS

| 4,546,769 | A | * | 10/1985 | Planck et al. ............... 606/231 |
| 5,690,014 | A | * | 11/1997 | Larkin ........................... 87/13 |
| 2004/0122454 | A1 | * | 6/2004 | Wang et al. ................. 606/152 |
| 2004/0198127 | A1 | * | 10/2004 | Yamamoto et al. ......... 442/408 |
| 2006/0051543 | A1 | * | 3/2006 | Imanari et al. ............. 428/35.7 |

FOREIGN PATENT DOCUMENTS

| JP | 1991-117208 | | 12/1991 |
| JP | 10-106229 | | 4/1998 |
| JP | 2002-119928 | | 4/2002 |
| JP | 2005287976 | A * | 10/2005 |

* cited by examiner

*Primary Examiner*—Shaun R Hurley
(74) *Attorney, Agent, or Firm*—Kratz, Quintos & Hanson, LLP

(57) ABSTRACT

A cleaning tool includes a cord-like structure formed from yarn, that includes at least in part thereof fine fibers of which the fineness of a single fiber is 1.1 decitex or lower, entwined into a cord shape so that the ends of the fibers are not exposed to the outside of the fabric while the total surface area is from 150000 to 2500000 $m^2$ per 1 $m^3$ and the apparent density is from 100000 to 700000 $g/m^3$. Such a cleaning tool is capable of cleaning the surface of an object that has irregularities and gaps even when the surface irregularities and gaps are very small.

9 Claims, 4 Drawing Sheets

 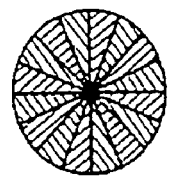 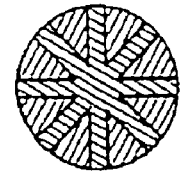
Fig. 3(a)　　Fig. 3(b)　　Fig. 3(c)
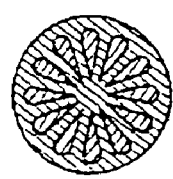 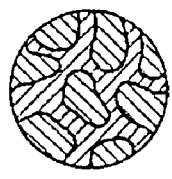 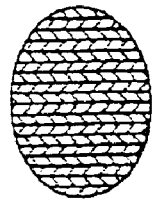
Fig. 3(d)　　Fig. 3(e)　　Fig. 3(f)
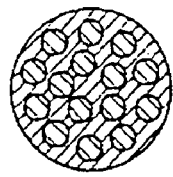 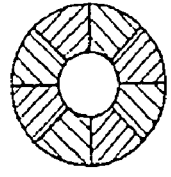 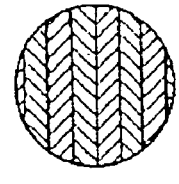
Fig. 3(g)　　Fig. 3(h)　　Fig. 3(i)
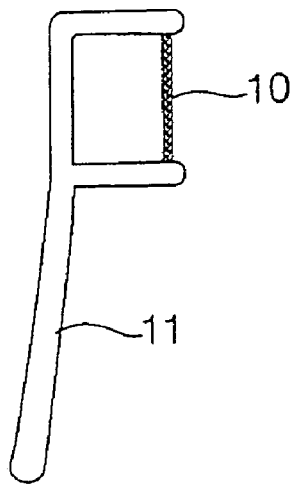 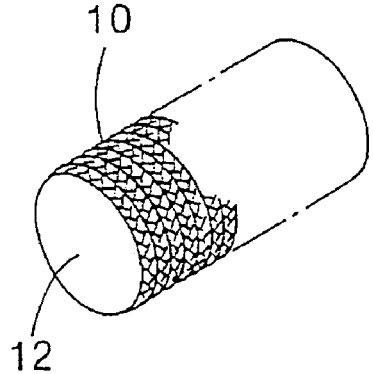
Fig. 4(a)　　　　　Fig. 4(b)

CLEANING TOOL

FIELD OF THE INVENTION

The present invention relates to a cleaning tool suited for cleaning of minute recessed portions.

BACKGROUND OF THE INVENTION

Staining of the parts of electronic apparatuses such as semiconductor components and magnetic recording media causes significant deterioration in the performance of the parts. Accordingly, it has been the practice to keep the surfaces of parts clean by wiping stain off the surface with hand using wiping cloth made of fine fibers.

Such an operation as shown in FIG. 5 is also practiced wherein recessed surfaces are cleaned with a pointed stick wrapped with a wiping tape 1a, that is, a narrow strip cut from the wiping cloth 1 described above. Alternatively, it has been proposed to wind the wiping tape 1a described above in a roll and press the wiping tape 1a against an object (hard disk, etc.) to be cleaned while unwinding the wiping tape 1a (Japanese Unexamined Patent Publication No. 10-106229, etc.).

However, as the electronic parts become smaller, with higher precision, recently it has been required to clean the inside of cylindrical objects having diameters of 1 to 2 mm or bumps and recesses about 1 mm across, such as the inside of a bearing for a hard disk motor and the terminals of liquid crystal display panel. The conventional wiping tape 1a is not capable of meeting these requirements.

In particular it is noted that thermal cutting has been used to cut the wiping tape 1a. Since thermal cutting cuts off fibers with heat, the ends of the fibers at both cut edges 2 of the wiping tape 1a are, once melted and then hardened, turned into hard lumps of resin, as shown in FIG. 6, that deprive the fabric of the characteristic softness. When the wiping tape 1a is cut to a width of 10 mm or less, for example, a proportion of the hardened edge portions 2 to the entire fabric becomes high enough to damage the surface portion to be cleaned or cause a problem, namely, that of the lumps of resin coming off and thereby generating dust. Also there has been a problem that the hardened portions have higher rigidity and therefore to do not readily comply with small ups and downs on the surface, resulting in insufficient cleaning performance.

The present invention has been made to solve these problems, and has an object of providing a high performance cleaning tool that is capable of cleaning any tiny surface irregularities and the inside of tiny recesses or gaps of the object to be cleaned.

SUMMARY OF THE INVENTION a first aspect of the present invention for achieving the object described above is a cleaning tool comprising a cord-like structure formed from yarn, that includes at least in part thereof fine fibers having fineness of single fiber of 1.1 decitex or lower, being entwined so that ends of fibers are not exposed to the outside of the fabric (e.g., cord-like structure or yarn), and with total surface area being from 150000 to 2500000 m$^2$ per 1 m$^3$ and apparent density being from 100000 to 700000 g/m$^3$.

A second aspect of the present invention is a particular type of the cleaning tool described above, wherein the cord-like structure is a knitted fabric or a braided cord. A third aspect of the present invention is that the cord-like structure is a knitted fabric that is formed by either circular knitting, tricot knitting, or flat knitting.

A fourth aspect of the present invention is that the cord-like structure has a width of 2 mm or less and thickness of 1 mm or less, and a fifth aspect of the present invention is a particular type of the cleaning tool wherein stitches (e.g., fibers) appearing on the surface of the cord-like structure are arranged in a direction inclined by an angle of 20° to 90° from the longitudinal direction of the cord-like structure.

BRIEF DESCRIPTION OF THE DRAWINGS

FIGS. 3(a) through 3(i) show various shapes of fibers of cleaning tapes used in the example described above.

FIGS. 4(a) and 4(b) show modes of using the example described above.

BEST MODES FOR CARRYING OUT THE INVENTION

Now preferred embodiments of the present invention will be described below.

Figure 1:
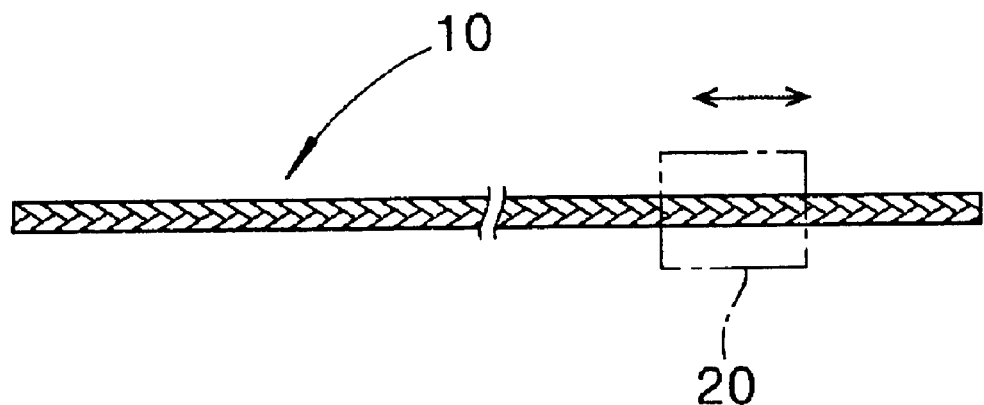
FIG. 1 shows an overview of an example of the present invention.

FIG. 1 shows a cleaning tool according to an embodiment of the present invention. This cleaning tool comprises a cord-like structure 10 that is formed from yarn which includes, at least in part thereof, particular fine fibers entwined to form a cord so that ends of fibers are not exposed to the outside of the fabric (e.g., cord-like structure or yarn).

Figure 2:
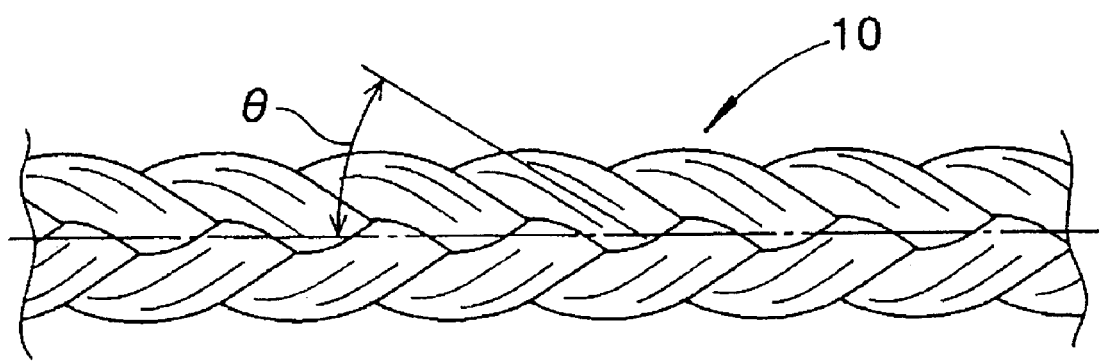
FIG. 2 is a partially enlarged view of the example described above.

The cord-like structure 10 may be, in addition to a knitted fabric that is formed by either circular knitting, tricot knitting or flat knitting, a braided cord formed by entwining fibers, not by knitting. The cord-like structure also includes plain yarn itself that is not braided or knitted, such as folded yarn that is twisted and covered yarn. The cord-like structure 10 is preferably constituted so that stitches (e.g., fibers) appearing on the surface of the cord-like structure are arranged in a direction inclined by a certain angle from the longitudinal direction of the cord-like structure 10, which produces higher cleaning effect when wiping by running the cleaning tool in the longitudinal direction of the cord-like structure. Specifically, the cord-like structure is preferably knitted or braided so that the angle θ (refer to FIG. 2 showing a partial enlargement of FIG. 1) is from 20° to 90°. Examples are a plain stitch structure produced with a circular knitting machine, or a tricot fabric produced with a tricot machine. In case plain yarn is used, such as folded yarn or covered yarn, it is preferable to give a constant angle, similar to θ described above, from 20° to 90° by twisting or covering. In the case of an ordinary braided cord, in contrast, the angle θ is almost 0° (all stitches are substantially aligned in the longitudinal direction) and therefore cleaning effect tends to be a little lower when wiping by running the cleaning tool in the longitudinal direction.

The yarn that constitutes the cord-like structure 10 must use, at least in part thereof, fine fibers in order to ensure desired cleaning effect. Fineness of the fine fiber is determined in accordance with the object of which the surface is to be cleaned. In order to clean minute portions of objects such as a computer keyboard, telephone, cell phone and jewelry, the cord-like structure may be formed from yarn made of fine fiber of which fineness of a single fiber is 1.1 decitex or less. When more precision is required, such as when cleaning the inside of a bearing for a hard disk motor or the terminals of a liquid crystal display panel, ultra-fine fibers of which the fineness of a single fiber is 0.6 decitex or less, particularly around 0.1 decitex, are preferably used. There is no limitation to the material of the fibers, as long as the material includes synthetic filament such as polyamide, polyester, polypropylene and polyethylene.

Such a fine fiber can be made by processing a conjugate fiber that comprises two or more components bonded together forming a plurality of segments into a single fiber, so as to turn the conjugate fiber into split fibrils. The split fibril can be formed by removing one of the components by dissolving or decomposition, swelling the component by means of a swelling agent, contracting the component by means of a shrinking agent, or deforming and shrinking the component by heating. Physical splitting of the plurality of components by friction or striking may also be employed. It is particularly preferable to dissolve and remove one of the components by using sodium hydroxide solution thereby to split the fibers, which can render the resultant cord-like structure 10 soft to touch without hard contact. The splitting process is usually carried out after forming the yarn, that includes the conjugate fibers at least in a part thereof, into a cord shape.

FIGS. 3(a) through (i) show examples of the cross section of conjugate fiber suitable for making split fibrils. Splitting the fibers shown in FIG. 3(a) and FIG. 3(f), for example, produces fine fibers of which two components both have flat configuration. The fiber shown in FIG. 3(b) has the two components arranged alternately in the form of a number of fan-shaped segments. The fiber shown in FIG. 3(c) combines one component formed in radial shape and the other component formed in fan shape. FIG. 3(d) shows an example where one component formed in a radial shape is integrated in the other component. FIG. 3(e) shows an example where one component is dispersed irregularly like islands in the other component. FIG. 3(g) shows an example where one component is integrated as multiple cores in the other component. FIG. 3(h) shows an example where two components are arranged alternately in a circle, with the central portion being hollow. FIG. 3(i) shows an example where two components are arranged alternately in one direction. The fine fiber can be formed in any other compound constitution as well as those described above, as long as each component is divided in segments. Among these, the fine fiber comprising the conjugate fibers shown in FIG. 3(b) and FIG. 3(c) have sharp edges that improve the cleaning effect, and are therefore preferable.

The cord-like structure 10 used for the cleaning tool of the present invention has a certain level of cleaning effect as long as the fine fibers are used in at least part thereof. In case a knitted fabric is used for the cord-like structure 10, for example, either the whole structure may be formed from a yarn made of the fine fiber, or a yarn made of the fine fiber and an ordinary yarn may be mixed and knitted in predetermined proportions. Sufficient cleaning effect can be achieved when the proportion of the fine fiber is 30% or higher.

The size of the cord-like structure 10 is, when formed in a band shape, preferably 2 mm or less in width and 1 mm or less in thickness. When the cord-like structure 10 is a round cord, it preferably has a diameter of 2 mm or less. Making the cord-like structure 10 with such a small size makes it possible to effectively clean the inside of small cylinders and surfaces having minute irregularities. In case the cord-like structure 10 is made in tubular shape having annular cross section by circular knitting or the like, it is preferable that width and thickness of this cord that is placed on a horizontal surface and is flattened are in the ranges described above.

For the cord-like structure 10 to have good cleaning performance, it must be made with knitting conditions (types of yarn and needle, number of courses, etc.) such that the total surface area is in a range from 150000 to 2500000 $m^2$ per 1 $m^3$. When the total surface area is below 150000 $m^2$ per unit volume, sufficient cleaning performance cannot be achieved. When the total surface area exceeds 2500000 $m^2$ per unit volume, manufacturing cost becomes higher while the cleaning performance does not improve.

In order for the cord-like structure 10 to have compliance and good contact with the surface of object to be cleaned, it must be made with such knitting conditions that the apparent density is from 100000 to 700000 $g/m^3$. When the apparent density is below 100000 $g/m^3$, sufficient cleaning performance cannot be achieved due to the presence of too much void. When the apparent density exceeds 700000 $g/m^3$, sufficient cleaning performance cannot be achieved because the fibers are crowded too close to each other.

The cord-like structure 10 thus obtained is cut to proper length and used in the cleaning tool. To clean the inside of cylindrical bodies (inner diameter 1 to 2 mm) such as the bearing for hard disk motor, the inside can be cleaned by inserting and sliding the cord-like structure 10 through the hollow space of the cylindrical body 20 as indicated by the imaginary line in FIG. 1.

The cord-like structure 10 may also be stretched between ends of a substantially C-shaped portion of a fixture 11 as shown in FIG. 4(a), for cleaning of narrow gaps.

Moreover, as shown in FIG. 4(b), the cord-like structure 10 may be wound around a cylindrical roll 12 with every turn placed close to the adjacent one without a gap, to make a cleaning roll. The cleaning roll 12 is rolled over the surface to be cleaned such as a hard disk. This cleaning operation may be carried out while supplying an alkali solution, alcohol or a polishing liquid that includes a polishing agent onto the surface to be cleaned, to make the cleaned surface smoother.

The cleaning tool of the present invention does not damage the objects to be cleaned nor generate dust of hardened resin comming off the ends of thermally cut fibers, since the cleaning tool comprises the cord-like structure 10 formed from yarn that includes a specific fine fiber in at least a part thereof, and is formed into the shape of a cord so that the ends of the fibers are not exposed to the surface of the cord, as described above. Also, because the cord has a special structure having total surface area per unit volume and apparent density being set within predetermined ranges, it is made possible to easily and effectively clean surfaces that have minute irregularities, small gaps, and the inside of small cylindrical objects such as a miniature bearing housing.

When the cleaning tool of the present invention is used in a semiconductor manufacturing process or the like that requires high precision, it is preferable that dust generation from the cord-like structure 10 that constitutes the cleaning tool is controlled so that particulates measuring 0.3 to 5.0 µm across are substantially unobservable. The expression of "substantially unobservable" means that, upon measuring dust generation from a sample three times or more according to tumbling method in compliance to EES-RP-CC-003-87-T standard, an average number of particulates observed measuring 0.3 to 5.0 μm across is 10 or less.

EXAMPLES

Examples of the present invention will be described below in conjunction with Comparative Examples.

Example 1

A twist of 110 T/M in direction S was applied to three filaments of splittable conjugate fiber having the cross section shown in FIG. 3(c) (a radially disposed component of 6-nylon and an 8-segment fan-shaped component of polyester combined, with a fineness of 56 decitex/25 filaments), to make a plied yarn of 168 decitex/75 filaments. Three strings of the plied yarn were put together and knitted into a plain stitch structure using a circular knitting machine (shuttle diameter about 5 mm, three needles), with the resultant cord-like knitting being wound into the form of hank. Then denier reduction was applied under the conditions described below with a yarn dyeing machine, followed by washing in warm water of 60° C., dehydration and drying.

[Conditions of Denier Reduction]

| | |
|---|---|
| Processing liquid: | Aqueous NaOH solution |
| Concentration: | 29 g/liter |
| Temperature: | 98° C. |
| Duration: | 40 minutes |

Volume reduction ratio resulting from the denier reduction process was 12%, and the three conjugate fibers that constitute the knitting fabric were each divided into eight polyester fibers and one 6-nylon fiber. The fineness of single polyester fiber was about 0.16 decitex.

The cord-like knitting described above was cut with heat to a length of 1 m, washed in ion-exchanged water, and then dried. The cord-like knitting thus obtained had a cylindrical shape of about 1 mm in diameter, without any ends of cut fibers exposed to the outside that serves as the cleaning surface, and with inclined line of stitches (loop) being arranged regularly.

Example 2

A cord-like knitting was obtained similarly to Example 1 except for using six needles in the circular knitting machine of Example 1. In this cord-like knitting, that had the form of a tape about 2.8 mm in width and about 0.9 mm in thickness, too, the ends of cut fibers were not exposed to the outside that served as the cleaning surface and the inclined lines of stitches (loop) were arranged regularly.

Example 3

Figure 7:
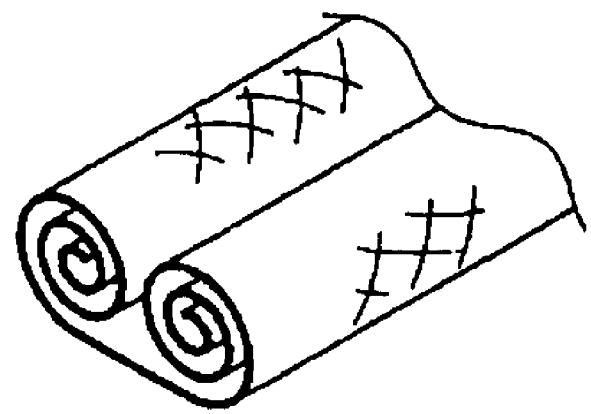
FIG. 7 is a diagram explaining Example 3 of the present invention.

A cord-like knitting was obtained similarly to Example 1 except for using three strings of the plied yarn of Example 1 put together and knitted into a grey fabric with a flat knitting machine (18 G, knitting width 30 mm). In this cord-like knitting that had a form of tape about 5 mm in width and about 2.5 mm in thickness (curled in the direction of width as shown in FIG. 7), too, the ends of cut fibers were not exposed to the outside that serves as the cleaning surface and inclined line of stitches (loop) were arranged regularly.

Example 4

Primary twist of 900 T/M in direction S was applied to a splittable conjugate fiber (110 decitex/50 filaments) similar to that of Example 1 to make plied yarn. Two strings of this yarn were plied together by applying a twist of 600 T/M in a direction Z, opposite to that of the primary twist, thereby making a folded yarn. The folded yarn was subjected to denier reduction and the following processes similar to those of Example 1 thereby to obtain folded yarn constituted from fine fibers. In this folded yarn thus obtained, that was formed in a form of tape about 0.36 mm in width and about 0.18 mm in thickness, too, the ends of cut fibers were not exposed to the outside that served as the cleaning surface and inclined line of stitches were arranged regularly.

Example 5

Splittable conjugate fibers (110 decitex/50 filaments) similar to those of Example 1 were used as a core thread and a sheath thread so as to make covered yarn with 1000 turns/m of covering. The covered yarn was subjected to denier reduction and the following processes similarly to those of Example 1, thereby to obtain covered yarn constituted from fine fibers. In this covered yarn thus obtained, having cylindrical shape with diameter of about 0.53 mm, too, the ends of cut fibers were not exposed to the outside that served as the cleaning surface and inclined line of stitches were arranged regularly.

Comparative Example 1

Cord-like knitting was obtained similarly to Example 1 except that, instead of the splittable conjugate fiber, synthetic filament of round cross section made solely of polyester was used. Volume reduction ratio in the denier reduction process was 12% and the fineness of the single polyester fiber was about 1.9 decitex. In this cord-like knitting, too, the ends of cut fibers were not exposed to the outside that served as the cleaning surface and inclined line of stitches (loop) were arranged regularly.

Comparative Example 2

Splittable conjugate fiber filament similar to that of Example 1 was knitted into an interlock structure using a circular knitting machine (shuttle diameter about 110 cm, 40 gauge) so as to make a grey fabric (wale 60, course 60) that was then opened. The grey fabric was immersed in a processing solution under the conditions described below and left to stand still to undergo the denier reduction process, followed by washing in warm water of 80° C., dehydration, and drying.

[Conditions of Denier Reduction]

| Processing liquid: | |
| --- | --- |
| Benzyl alcohol | 25% |
| Nonionic emulsifier | 2% |
| Water | 73% |
| Temperature: | 25° C. |
| Duration: | 5 minutes |

The knitted fabric after processing showed shrunk stitches (wale 75, course 75). The conjugate fiber that constituted the knitted fabric was divided into eight polyester fibers and one 6-nylon fiber, with the fineness of the single polyester fiber being about 0.13 decitex.

Figure 5:
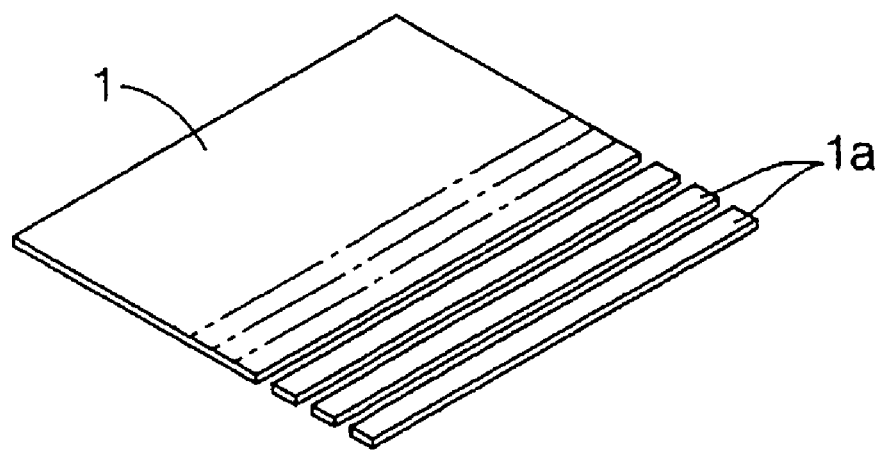
FIG. 5 shows an example of a cleaning tool of the prior art.
Figure 6:
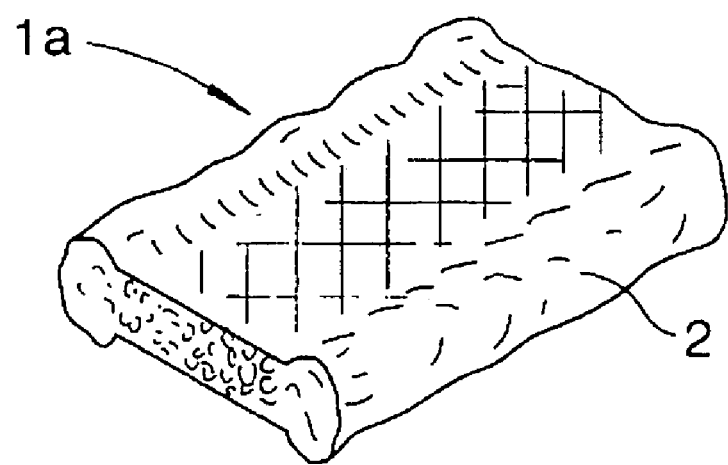
FIG. 6 is a diagram explaining the problems in the prior art.

The knitted fabric described above was cut with heat into thin, long cord 3 mm wide and 1 m long as shown in FIG. 5, washed in ion-exchanged water, and then dried. The cord-like knitting thus obtained was a tape about 3 mm wide and 0.4 mm thick, and had hardened bulges (about 0.5 mm wide, refer to FIG. 6) formed on both edges of the width during thermal cutting.

Comparative Example 3

Cord-like knitting was obtained similarly to Example 2 except that, instead of the splittable conjugate fiber, a textured yarn, made by applying false twisting to the synthetic filament of round cross section that was made solely of polyester, was used. The cord-like knitting had a

[Total Surface Area and Apparent Density]

[Equation 1]

$$\text{Total surface area} = \frac{S \times (D/d)}{V} \quad (1)$$

$$\text{Apparent density} = \frac{D/10000}{V} \quad (2)$$

In the formulae (1) and (2),

D: Total decitex value of cord-like structure

V: Volume (m³) per 1 m of cord-like structure

S: Total surface area (m²) per 1 m of component fiber d: Decitex value of component fiber

TABLE 1

| | Example 1 | Example 2 | Example 3 | Example 4 | Example 5 |
| --- | --- | --- | --- | --- | --- |
| Fineness of single fiber (dtex) | 0.16 | 0.16 | 0.16 | 0.16 | 0.16 |
| Stitch angle θ | 30 | 25 | 25 | 10 | 38 |
| Cleaning performance | ◎ | ◎ | ◎ | ○ | ◎ |
| Scratch on wiped surface | None | None | None | None | None |
| Duct generation (Mean count) | 1.2 | 1.1 | 1.7 | 1.3 | 1.2 |
| Total surface area (m²/1 m³) | 708,790 | 376,590 | 329,600 | 536,280 | 160,710 |
| Apparent density (g/m³) | 503,980 | 267,860 | 239,940 | 378,550 | 113,100 |

TABLE 2

| | Comparative Example 1 | Comparative Example 2 | Comparative Example 3 |
| --- | --- | --- | --- |
| Fineness of single fiber (dtex) | 1.9 | 0.13 | 1.2 |
| Stitch angle θ | 30 | 30 | 30 |
| Cleaning performance | X | ◎ | X |
| Scratch on wiped surface | None | Observed | None |
| Duct generation (Mean count) | 1.5 | 20 | 1.8 |
| Total surface area (m²/1 m³) | 132,480 | 421,200 | 34,700 |
| Apparent density (g/m³) | 609,908 | 325,000 | 99,260 |

The cleaning tool of the present invention, since the cord-like structure of special constitution is used as described above, allows convenient cleaning operations to easily and effectively clean even minute surface irregularities and gaps by simply applying the cord-like structure of the present invention into contact with the minute recesses and the inside of the gaps.

In case a knitted fabric or braiding is used as the cord-like structure in the present invention, a structure in which the ends of fibers are not exposed to the outside can be easily obtained. Among such structures, one formed by either circular knitting, tricot knitting or flat knitting is more preferable in view of the cleaning effect.

Use of the cord-like structure of the present invention measuring 2 mm or less in width and 1 mm or less in thickness is preferable since it makes it easier to clean minute gaps and surface irregularities.

Use of the cord-like structure of the present invention wherein stitches appearing on the surface of the cord-like structure are arranged in a direction inclined by an angle of 20° to 90° from the longitudinal direction of the cord-like structure is preferable since such a constitution makes it possible to achieve good cleaning effect by simply moving the cleaning tool in the longitudinal direction of the cord-like structure.

The invention claimed is:

1. A cord-like structure for cleaning, comprising a yarn knitted or braided such that ends of the yarn are not exposed to the outside of the cord-like structure, the yarn including at least in part thereof fine fibers having a fineness of a single fiber of 1.1 decitex or lower, the cord-like structure having a total surface area of from 150,000 to 2,500,000 m² per 1 m³ and an apparent density of from 100,000 to 700,000 g/m³.

2. The cord-like structure for cleaning according to claim 1, wherein said cord-like structure is a knitted yarn formed by either circular knitting, tricot knitting or flat knitting.

3. The cord-like structure for cleaning according to claim 1, wherein sizes of said cord-like structure are set to 2 mm or less in width and 1 mm or less in thickness.

4. The cord-like structure for cleaning according to claim 2, wherein sizes of said cord-like structure are set to 2 mm or less in width and 1 mm or less in thickness.

5. The cord-like structure for cleaning according to claim 1, wherein fibers appearing on the surface of the cord-like structure are arranged in a direction inclined by an angle of 20° to 90° from the longitudinal direction of the cord-like structure.

6. The cord-like structure for cleaning according to claim 2, wherein fibers appearing on the surface of the cord-like structure are arranged in a direction inclined by an angle of 20° to 90° from the longitudinal direction of the cord-like structure.

7. The cord-like structure for cleaning tool according to claim 1, wherein at least in part the fine fibers have a fineness of a single fiber of 0.6 decitex or lower.

8. A cord-like structure for cleaning, comprising a plain yarn that is not knitted or braided, the yarn including at least in part thereof fine fibers having fineness of single fiber of 1.1 decitex or lower, the cord-like structure having a total surface area of from 150,000 to 2,500,000 m² per 1 m³ and apparent density of from 100,000 to 700,000 g/m³.

9. The cord-like structure for cleaning according to claim 8, wherein sizes of said cord-like structure are set to 2 mm or less in width and 1 mm or less in thickness.

* * * * *